United States Patent
Romero et al.

[19]

[11] Patent Number: 6,079,758
[45] Date of Patent: Jun. 27, 2000

[54] TOOL HOLDING APPARATUS FOR PERSONS WITH LIMITED USE OF HANDS

[76] Inventors: Ramiro R. Romero, 219 Ellingbrook Dr., Montebello, Calif. 90640; Cynthia M. Deslarzes, 20239 Heather Cliff, #8, Malibu, Calif. 90265; Ron Anson, 414 S. Cliffwood La., Los Angeles, Calif. 90049

[21] Appl. No.: 09/131,624

[22] Filed: Aug. 10, 1998

Related U.S. Application Data

[63] Continuation-in-part of application No. 08/708,192, Sep. 6, 1996, Pat. No. 5,791,705.

[51] Int. Cl.$^7$ .................................. A45F 5/00; A61F 2/54
[52] U.S. Cl. ................................. 294/25; 30/298; 224/218
[58] Field of Search .................. 294/1.1, 25; 15/437, 15/443; 30/298; 224/218, 219, 222, 267; 401/8; 623/65

[56] References Cited

U.S. PATENT DOCUMENTS

| | | | |
|---|---|---|---|
| 488,538 | 12/1892 | Byor | 30/298 X |
| 828,798 | 8/1906 | Anderson | 30/298 X |
| 862,734 | 8/1907 | Hendricks | 30/298 |
| 1,181,527 | 5/1916 | Hooper | 30/298 |
| 4,165,896 | 8/1979 | Hunt | 294/25 |
| 5,597,189 | 1/1997 | Barbee | 294/25 |

*Primary Examiner*—Johnny D. Cherry

[57] ABSTRACT

An apparatus to assist in gripping a hand-held tool comprises a substantially rigid engaging portion for removably clipping the apparatus to an arm. The engaging portion has a base member and an arcuate member and a linear member to simultaneously engage a portion of the arm. The arcuate member has a first end extending essentially perpendicularly therefrom and is adjustably connected to the base member. A first end of the linear member extends upwardly from an opposite end of the base member. The arcuate member and the linear member are in an essentially parallel relationship along their entire extents. The linear member further has a free second end. A tool receiving portion includes a pair of outwardly extending side walls, an open bottom end and an open top end and is integrally formed with the linear member of the engaging portion so that the tool receiving portion remains in a coplanar relationship with the first linear member of the engaging portion. A means for securing the tool to the tool receiving portion includes an elastic band.

6 Claims, 4 Drawing Sheets

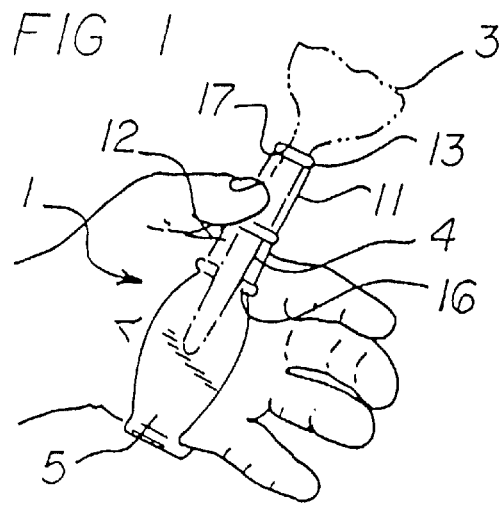
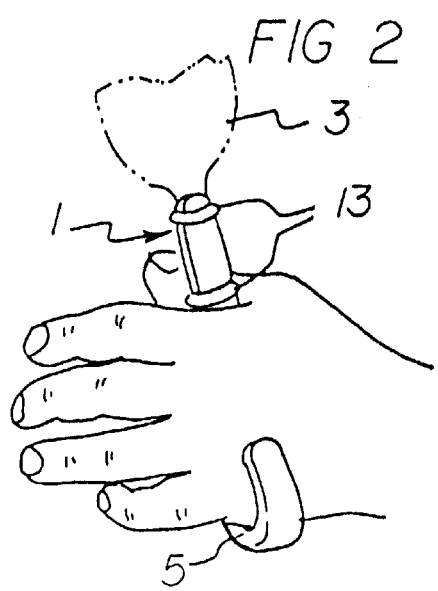
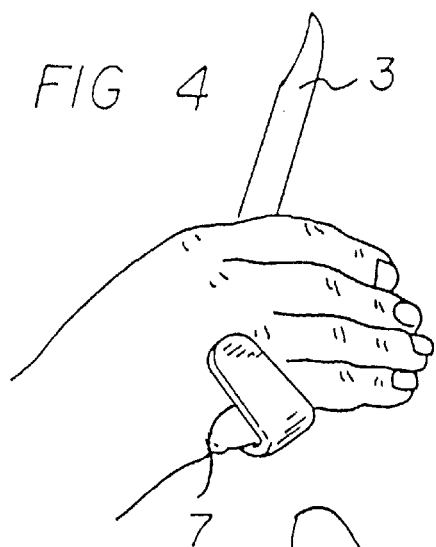
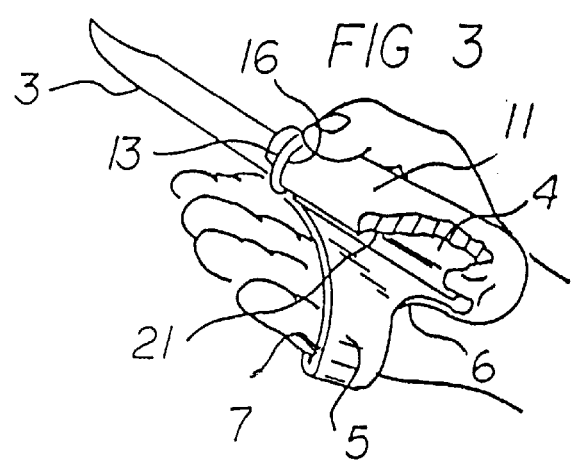
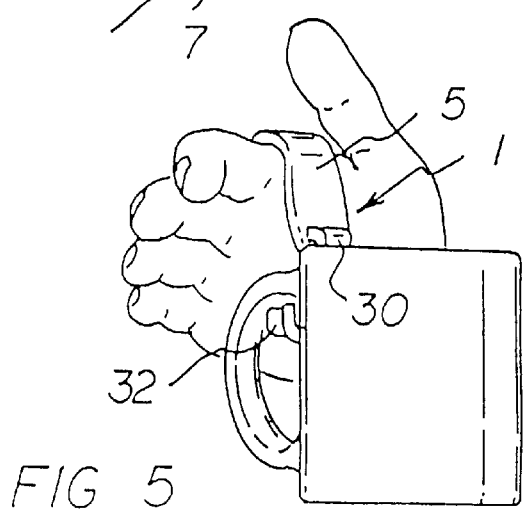
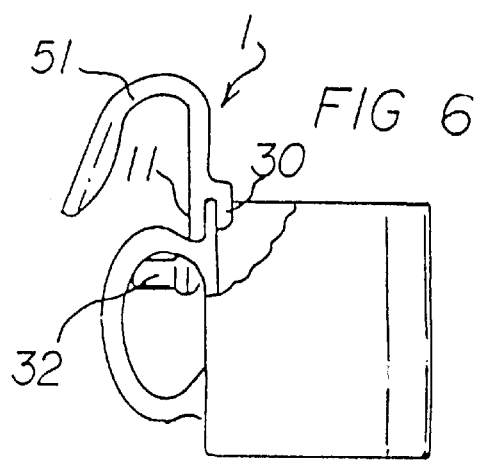

TOOL HOLDING APPARATUS FOR PERSONS WITH LIMITED USE OF HANDS

BACKGROUND OF THE INVENTION

This application is a continuation-in-part of application Ser. No. 08/708,192 filed Sep. 6, 1996, now U.S. Pat. No. 5,791,705 and incorporated herein by reference.

FIELD OF THE INVENTION

The present invention relates to a tool holding apparatus for persons with limited use of hands and more particularly pertains to assisting persons with limited gripping ability to use hand-held tools with a tool holding apparatus for persons with limited use of hands.

DESCRIPTION OF THE PRIOR ART

The use of tool holding devices is known in the prior art. More specifically, tool holding devices heretofore devised and utilized for the purpose of holding tools for individuals are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,606,484 to Winter; U.S. Pat. No. 5,086,818 to Bendt; U.S. Pat. No. 2,903,024 to Lohse; U.S. Pat. No. 4,287,921 to Sanford; U.S. Pat. No. 4,421,147 to Cannella; and U.S. Pat. No. 4,130,149 to Hausam.

While these devices fulfill their respective, particular objective and requirements, the aforementioned patents do not describe a tool holding apparatus for persons with limited use of hands for assisting persons with limited gripping ability to use hand-held tools.

In this respect, the tool holding apparatus for persons with limited use of hands according to the present invention substantially departs from the conventional concepts and designs of the prior art, and in doing so provides an apparatus primarily developed for the purpose of assisting persons with limited gripping ability to use hand-held tools.

Therefore, it can be appreciated that there exists a continuing need for new and improved tool holding apparatus for persons with limited use of hands which can be used for assisting persons with limited gripping ability to use hand-held tools. In this regard, the present invention substantially fulfills this need.

SUMMARY OF THE INVENTION

In the view of the foregoing disadvantages inherent in the known types of tool holding devices now present in the prior art, the present invention provides an improved tool holding apparatus for persons with limited use of hands. As such, the general purpose of the present invention, which will be described subsequently in greater detail, is to provide a new and improved tool holding apparatus for persons with limited use of hands and method which has all the advantages of the prior art and none of the disadvantages.

To attain this, the present invention essentially comprises a hand-engaging portion for removably engaging a portion of a palm and a portion of a back of a hand. A tool-receiving portion is coupled to the hand-engaging portion and receives the hand-held tool. Means for securing the handheld tool to the tool-receiving portion is also provided. The hand-engaging portion defines at least one groove for receiving the means for securing.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tool holding apparatus for persons with limited use of hands which has all the advantages of the prior art tool holding devices and none of the disadvantages.

It is another object of the present invention to provide a new and improved tool holding apparatus for persons with limited use of hands which may be easily and efficiently manufactured and marketed.

It is a further object of the present invention to provide a new and improved tool holding apparatus for persons with limited use of hands which is of durable and reliable construction.

An even further object of the present invention is to provide a new and improved tool holding apparatus for persons with limited use of hands which is susceptible of a low cost of manufacture with regard to both materials and labor, and which accordingly is then susceptible of low prices of sale to the consuming public, thereby making such a tool holding apparatus for persons with limited use of hands economically available to the buying public.

Even still another object of the present invention is to provide a new and improved tool holding apparatus for persons with limited use of hands for assisting persons with limited gripping ability to use hand-held tools.

Lastly, it is an object of the present invention to provide a new and improved tool holding apparatus for persons with limited use of hands including a hand-engaging portion for removably engaging a portion of a palm and a portion of a back of a hand. A tool-receiving portion is coupled to the hand-engaging portion and receives the hand-held tool. Means for securing the hand-held tool to the tool-receiving portion is also provided. The hand-engaging portion defines at least one groove for receiving the means for securing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIGS. 1 and 2 illustrate perspective views of one embodiment of the present invention.

FIGS. 3 and 4 illustrate perspective views of an alternate embodiment of the present invention.

FIG. 5 illustrates a perspective view of a third embodiment of the present invention that is adapted to aid one in the utilization of a cup.

FIG. 6 illustrates a side elevational view of how the third embodiment of the present invention attaches to the cup.

The same reference numerals refer to the same parts throughout the various Figures.

DETAILED DESCRIPTION OF THE INVENTION

Figure 7:
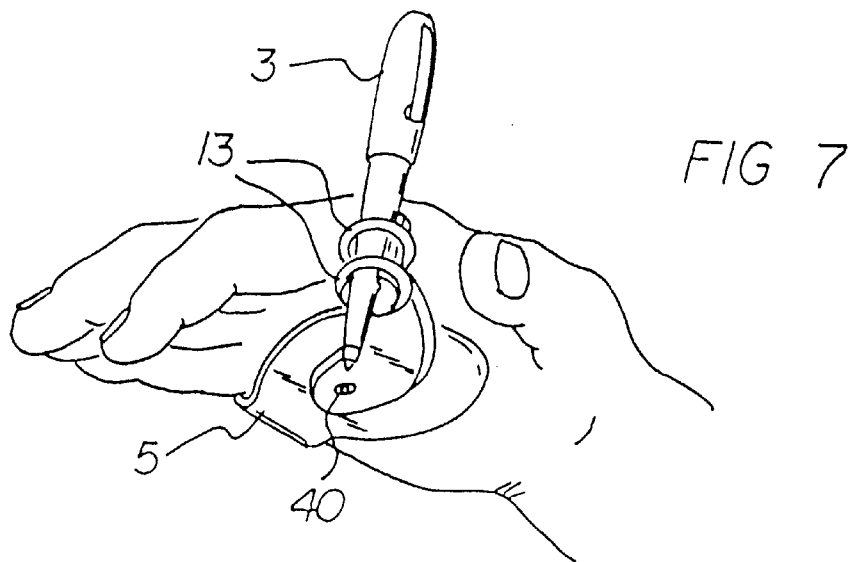
FIG. 7 illustrates a perspective view of a fourth embodiment of the present invention.

Although the disclosure hereof is detailed and exact to enable those skilled in the art to practice the invention, the physical embodiments herein disclosed merely exemplify the invention which may be embodied in other specific structures. The scope of the invention is defined in the claims appended hereto. The basic form of the invention is shown in FIGS. 1 through 14.

It should be noted that the hand shown in the figures is shown very sketchily and in phantom because they represent either the back of the hand, the palm of the hand and may also represent either hand. Although the device is shown mounted on a hand, it may also be mounted across the knuckles of the hand or if the individual lacks effective hands, it may be mounted on a portion of one's arm. If the person lacks effective arms and has sufficient leg mobility, it is even possible to modify the hand engaging portion of this device so as to be adapted to couple to one's leg.

It should also be noted that the term "tool" encompasses a wide variety of devices. Although the figures show a comb, knife, cup and pen, these devices are merely illustrative of an unlimited range of tools that may be held by the present invention. For example, a tool may include, inter alia, an eating utensil, for example a fork, spoon or knife, a shaving utensil, for example a razor, a hairbrush, a comb, a toothbrush, a cup, a typing instrument employed for manipulating a keyboard or typewriter, a writing utensil, for example a pen or pencil, and other tools used in life.

FIGS. 1 and 2 illustrate perspective views of one embodiment of the present invention. The apparatus 1, to assist in gripping a hand-held tool, includes a hand-engaging portion 5 coupled to a tool-receiving portion 11. The hand engaging portion 5 is configured to simultaneously engage at least a portion of a palm of the hand and a back of the hand. As shown in the Figures, the hand engaging portion has a first linear member with a first surface and a second linear member with a second surface to simultaneously engage a portion of the palm of the hand and a portion of the back of the hand, respectively. The linear members remain in parallel relationship along an entire extent thereof and the second linear member is equipped with a free second end. By sliding one's hand into the engaging portion 5 and applying slight pressure so that the engaging portion grips the side portion of the palm extending from the little finger, the improved tool-gripping apparatus 1 comprising the present invention easily engages and disengages from a hand with minimal effort. In fact, the hand-engaging portion 5 "clips" to the user's hand and may be coupled to the user's hand with minimal effort even for one with limited hand movement. It will be understood by those skilled in the art that the embodiments shown in FIGS. 1, 2, 3, 4 and 7 through 9 may be adapted accordingly so as to have the hand-engaging portion receive, or clip to, the portion of the hand between the thumb and index finger as illustrated in FIGS. 5 and 6.

The apparatus 1 may be manufactured by employing a substantially rigid material, for example, plastic, that is flexible, yet durable. Conventional manufacturing techniques, such as injection molding and other molding techniques, may be employed to make the tool-gripping apparatus 1. It is preferred that the material used to make the improved gripping apparatus 1 be moldable and formable by the application of heat to the material, for example, with a heat gun or boiling water. Such moldable and formable material allows the hand-engaging portion 5 to be modified by the application of heat so as to enable the hand-engaging portion 5 to be adapted to fit snugly the hand of a user. Alternately, a type of metal may also be used in the fabrication of the apparatus.

The tool-receiving portion 11 is adapted to receive any number of different tools 3. This tool 3 typically includes a handle 4. As show in the Figures, the tool receiving portion is coupled to a second end of the first linear member of the hand engaging portion. The tool-receiving portion 11 includes a surface 12 for engaging said handle 4 of said tool. The present invention 1 also includes means 13 for removably securing the tool 3 to the tool-receiving portion 11. In the preferred embodiment, the means for securing 13 are elastic bands, for example O-rings. However, it will be understood by those skilled in the art that other conventional means for securing may be employed. It should be noted that different sized O-rings may be employed to accommodate different tools 3 with different handle sizes and shapes. For example, an O-ring of a first size may be employed to couple the present invention 1 to a comb 3 that has a handle with a relatively small diameter. An O-ring of a second size is employed to couple the present invention 1 to a hairbrush 3 having a handle with a larger diameter.

The tool-receiving portion 11 further defines an extension of the first linear member and at least one groove 16 for receiving said means for securing 13. In a preferred embodiment, the tool-receiving portion 11 defines at least two grooves, 16, 17, for receiving two means for securing 13.

In the preferred embodiment, the hand-engaging portion 11 engages the back of a hand, wraps around and extends across a portion of the palm of the hand. The tool-receiving portion 11 extends across a portion of the palm and beyond the palm. The tool-receiving portion 11 that extends beyond the palm defines at least one groove 16 for receiving the means for securing 13. Other portions of the tool-receiving portion 11 also may define a groove for receiving means for securing 13.

FIGS. 3 and 4 illustrate perspective views of an alternative embodiment of the present invention. In this embodiment, the hand-engaging portion 5 includes a first surface 6 for engaging the palm of the hand and a second surface 7 for engaging the back of the hand. The tool-receiving portion 11 forms a surface that substantially encloses the handle 4 of a tool 3. The tool-receiving portion 11 defines the surface in such a way as to snugly hold the handle of the tool. However, the tool-receiving portion 11 includes a channel 21 through which the tool may be removed from or received by said tool-receiving portion with slight force or pressure. In this embodiment, the tool-receiving portion 11 also defines a groove 16 for receiving the means for securing 13. For this embodiment, one means 13 for securing, for example the O-ring, is employed. As shown in FIGS. 3 & 4, the tool receiving portion of the present embodiment is integrally coupled at a central extent thereof to a second end of the second linear member of the hand engaging portion such that the tool receiving member remains in coplanar relationship with the first linear member of the hand engaging portion and further defines an obtuse angle therewith.

FIG. 5 illustrates a perspective view of an alternate embodiment of the present invention that is adapted to hold a cup. FIG. 6 illustrates a side elevational view of how the third embodiment of the present invention attaches to the cup. The present invention 1 includes the hand-engaging portion 5 and the tool-receiving portion 11. The means for securing 13 include a first flange 30, for example, a hook member, and a second flange 32, for example, a support protrusion or boss, that are disposed to hold said cup. In the preferred embodiment, the hook member 30 engages a rim of the cup, and the support boss 32, for example, a support protection or bass, engages the handle of the cup. In the preferred embodiment, the hook member 30 and the support boss 32 are integrally molded with said tool-receiving portion 11. To attach this embodiment of the present invention to a cup, one simple engages the hook member 30 to a position along the rim of the cup that is slightly offset from a position on the rim directly above the handle of the cup. One then positions the support boss 32 so that it engages the handle of the cup as it is moved into the aperture of the cup handle. FIG. 6 illustrates a side of the elevational view of how the third embodiment of the present invention attaches to the cup. The hook portion 30 and the support boss 32 are disposed to hold the cup and to prevent the cup from rotating away from the present invention.

This embodiment of the present invention is formed in an advantageous way so that the sides of the cup do not contact the hand. This is particularly advantageous for those persons having limited grip ability, whose skin in the palm is typically more sensitive than that of the average person. In this embodiment, although the palm comes in contact with the cup handle, it is not in direct contact with the sides of the cup, thereby preventing burning of the sensitive skin of the palm of such users.

Figure 8:
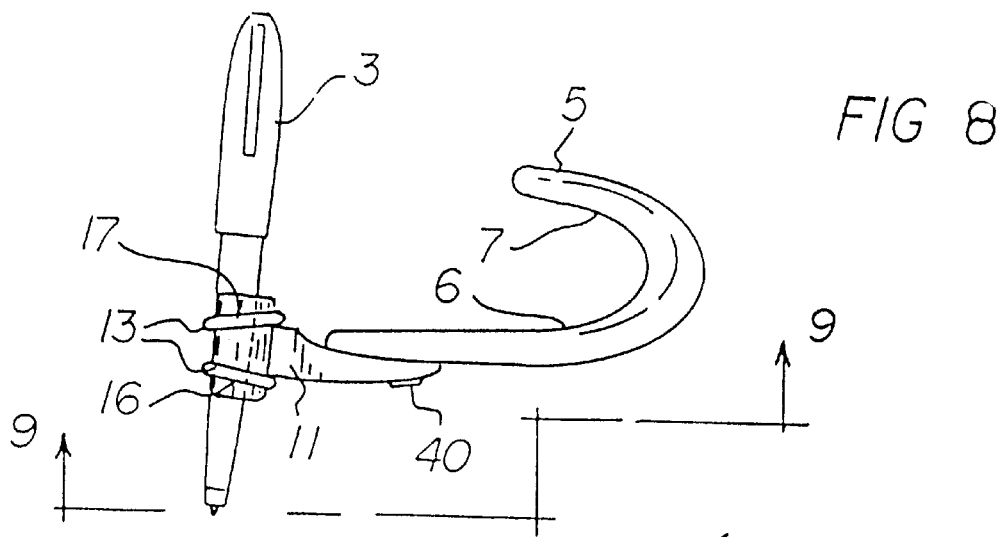
FIG. 8 illustrates a side elevational view of the fourth embodiment of the present invention.
Figure 9:
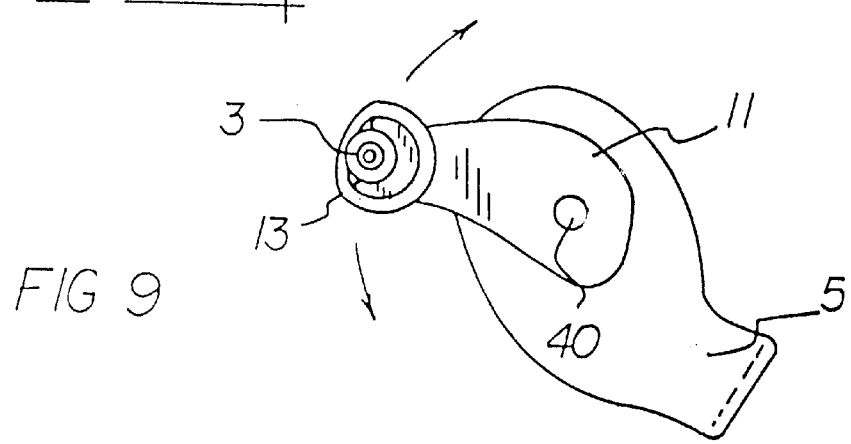
FIG. 9 illustrates a bottom plan view of the fourth embodiment of the present invention taken generally through line 9—9 of FIG. 8.

FIG. 7 illustrates a perspective view of a fourth embodiment of the present invention. FIG. 8 illustrates a side elevational view of the forth embodiment of the present invention. FIG. 9 illustrates a bottom plan view of the fourth embodiment of the present invention taken generally through line 9—9 of FIG. 8. In contrast to the embodiments illustrated thus far in FIGS. 1 through 6, the tool-receiving portion 11 is rotatably coupled to the first linear member of the hand-engaging portion 5 instead of being integrally molded as one piece. The tool-receiving portion 11 is rotatably coupled to the hand-engaging portion 5 via coupling means 40 that are well known in the art, for example, threaded nut and bolt, rivet, and the like. The means for coupling 40 should allow the tool-receiving portion 11 to rotate. The tool-receiving portion 11 in this embodiment defines grooves 16, 17 for receiving the means for securing 13. Also, the tool-receiving portion 11 defines a surface adapted to receive the tool. This embodiment is particularly useful for writing instruments, a typing instrument, a toothbrush, and eating utensils.

It will be noted by those skilled in the art, that the hand-engaging portion 5 may be rotatably coupled to the tool-receiving portion 11 by properly injection molding the hand-engaging portion with a hole of approximately a quarter of an inch in diameter and three-quarters of an inch in depth, and by injection molding the tool-receiving portion 11 with a stud of dimensions adapted to couple to the hole formed in the hand-engaging portion 5.

Figure 10:
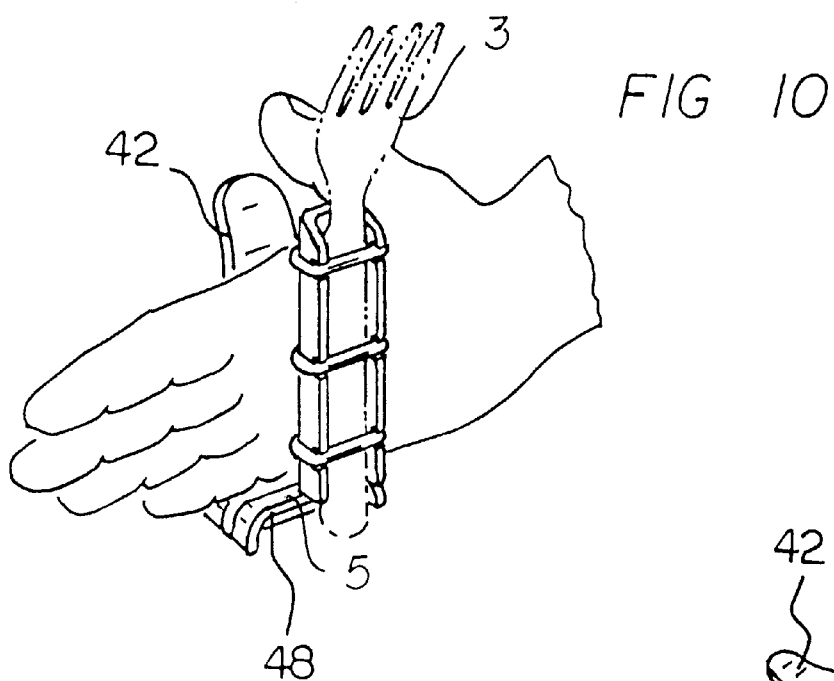
FIGS. 10, 11 and 12 illustrate perspective views of the fifth embodiment of the present invention.
Figure 11:
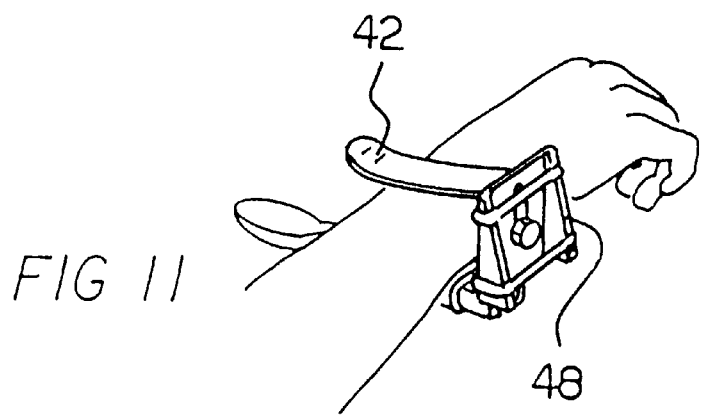
Figure 12:
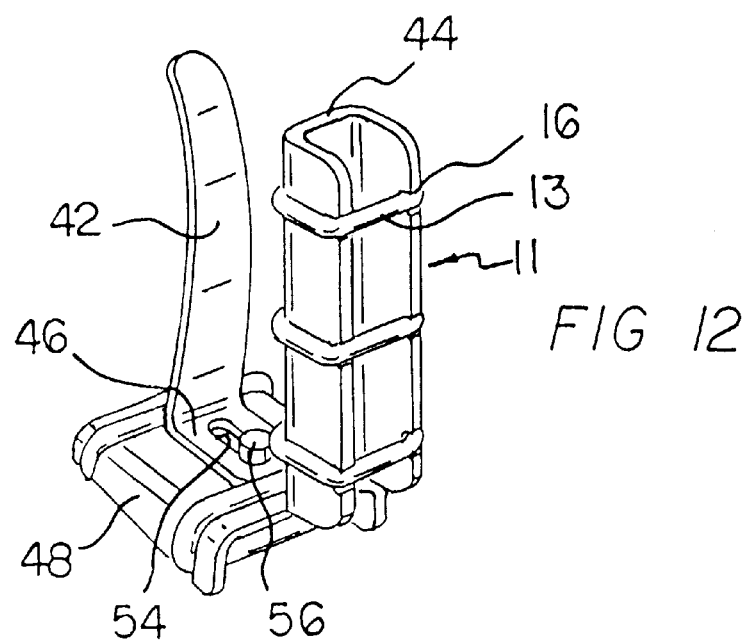
Figure 13:
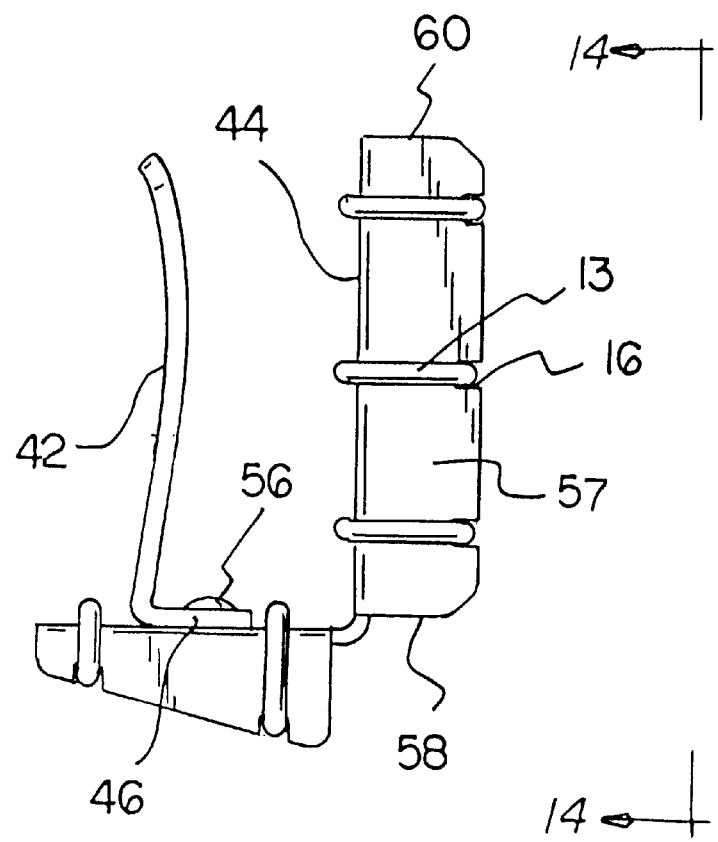
FIG. 13 illustrates a side elevational view of the fifth embodiment.
Figure 14:
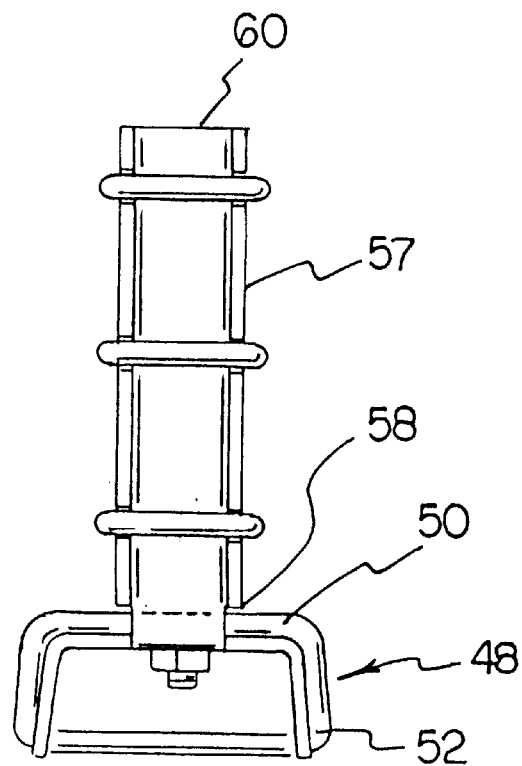
FIG. 14 illustrates an end view of the fifth embodiment as taken along line 14—14 of FIG. 13.

FIG. 10 illustrates a perspective view of a fifth embodiment of the present invention shown secured to a hand of the user. FIG. 11 illustrates a perspective view of the fifth embodiment of the present invention shown secured to a wrist of the user. FIG. 12 illustrates an isolated perspective view of the fifth embodiment of the present invention. FIG. 13 illustrates a side elevational view of the fifth embodiment of the present invention. FIG. 14 illustrates an end view of the fifth embodiment of the present invention taken generally from line 14—14 of FIG. 13. In contrast to the embodiments illustrated thus far in FIGS. 1–9, the substantially rigid engaging portion is for removably engaging an arm. FIGS. 10 and 11 show the rigid engaging portion 5 secured to the hand and the wrist respectively. The engaging portion 5 has an arcuate member 42 and a linear member 44 to simultaneously engage a portion of the arm. The arcuate member 42 has a first end 46 extending essentially perpendicularly therefrom and is adjustably connected to a base member 48. The base member 48 has a generally U-shaped cross-section. The base member 48 has a horizontal portion 50 and a pair of downwardly extending side portions 52. The first end 46 has a slot 54 formed therethrough for receiving a screw 56 therethrough from the base member 48 to facilitate adjustment of the arcuate member 42 with respect to the linear member 44 to vary a space disposed therebetween. This allows for the engaging portion 5 to be adjusted to accommodate various sizes of user's arms and wrists. A first end of the linear member 44 extends upwardly from an opposite end of said base member 48 such that the arcuate member 42 and the linear member 44 are in an essentially parallel relationship along an entire extent thereof. The linear member 44 further has a free second end. The engaging portion 5 removably clips said apparatus to said arm.

The tool receiving portion 11 includes a pair of outwardly extending side walls 57, an open bottom end 58 and an open top end 60. The tool receiving portion 11 is integrally formed with the linear member 44 of the engaging portion 5 such that the tool receiving member 11 remains in coplanar relationship with the linear member 44 of the hand engaging portion 5. The outwardly extending side walls 57 of the tool receiving portion 11 define at least one concentric groove 16 for receiving said elastic band 13. The tool receiving portion 11 defines a linear channel between the outwardly extending side walls 57 through which said tool 3 is placed into and taken out of said tool receiving portion 11.

The means that are provided for securing said tool 3 to said tool receiving portion 11 include at least one elastic band 13.

What is claimed is:

1. An apparatus to assist in gripping a hand-held tool, said apparatus comprising:

a) a substantially rigid engaging portion for removably engaging an arm; said engaging portion having a base member and an arcuate member and a linear member to simultaneously engage a portion of the arm, wherein the arcuate member has a first end extending essentially perpendicularly therefrom and being adjustably connected to said base member, a first end of the linear member extending upwardly from an opposite end of said base member such that the arcuate member and the linear member are in an essentially parallel relationship along an entire extent thereof, the linear member further having a free second end; wherein said engaging portion removably clips said apparatus to said arm;

b) a tool receiving portion including a pair of outwardly extending side walls, an open bottom end and an open top end, the tool receiving portion being integrally formed with the linear member of the engaging portion such that the tool receiving portion remains in a coplanar relationship with the linear member of said engaging portion; and c) means for securing said tool to said tool receiving portion including an elastic band.

2. The apparatus of claim 1, wherein the tool receiving portion is securable to a hand of the user.

3. The apparatus of claim 1, wherein the tool receiving portion is securable to a wrist of the user.

4. The apparatus of claim 1, wherein the outwardly extending side walls of the tool receiving portion define at least one concentric groove for receiving said elastic band.

5. The apparatus of claim 1, wherein said tool receiving portion defines a linear channel between the outwardly extending side walls through which said tool is placed into and taken out of said tool receiving portion.

6. The apparatus of claim 1, wherein the base member has a generally U-shaped cross-section, the base member having a horizontal portion and a pair of downwardly extending side portions, the first end of the arcuate member having a slot formed therethrough for receiving a screw from the horizontal portion therethrough to facilitate adjustment of the arcuate member with respect to the linear member to vary a space disposed therebetween.

* * * * *